US009715806B2

(12) United States Patent
Pham et al.

(10) Patent No.: US 9,715,806 B2
(45) Date of Patent: Jul. 25, 2017

(54) MONITORING OF FALL PROTECTION HARNESS USING A BODY AREA NETWORK

(71) Applicant: Honeywell International Inc., Morris Plains, NJ (US)

(72) Inventors: Hai D. Pham, Eden Priarie, MN (US); Steve D. Huseth, Plymouth, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/956,816

(22) Filed: Dec. 2, 2015

(65) Prior Publication Data

US 2017/0162020 A1    Jun. 8, 2017

(51) Int. Cl.
*G08B 21/02*    (2006.01)

(52) U.S. Cl.
CPC .................................. *G08B 21/02* (2013.01)

(58) Field of Classification Search
CPC .................................................... G08B 21/02
See application file for complete search history.

(56) References Cited

U.S. PATENT DOCUMENTS

| 7,106,205 B2 | 9/2006 | Graef et al. |
| 8,665,097 B2 | 3/2014 | Worthington et al. |
| 8,902,074 B2 | 12/2014 | Landry et al. |
| 2008/0021717 A1* | 1/2008 | Kaartinen .............. G06Q 10/00 705/303 |
| 2008/0021718 A1* | 1/2008 | Kaartinen ............ G06Q 10/087 705/325 |
| 2008/0161657 A1* | 7/2008 | Bullens ................ A61B 5/0031 600/301 |
| 2008/0164979 A1 | 7/2008 | Otto |
| 2012/0050036 A1 | 3/2012 | Landry et al. |
| 2013/0056302 A1 | 3/2013 | Bishop |
| 2015/0164238 A1 | 6/2015 | Benson et al. |

FOREIGN PATENT DOCUMENTS

EP    2314354 A2    4/2011

OTHER PUBLICATIONS

"European Application Serial No. 16198300.2, Extended European Search Report mailed Apr. 13, 2017", 9 pgs.

* cited by examiner

*Primary Examiner* — Leon Flores
(74) *Attorney, Agent, or Firm* — Schwegman Lundberg & Woessner, P.A.

(57) ABSTRACT

A system receives body area network (BAN) data and calculates an end of life of a fall protection harness as a function of the BAN data.

15 Claims, 10 Drawing Sheets

MONITORING OF FALL PROTECTION HARNESS USING A BODY AREA NETWORK

TECHNICAL FIELD

The present disclosure relates to fall protection harnesses, and in an embodiment, but not by way of limitation, monitoring fall protection harnesses using a body area network.

BACKGROUND

A body area network (BAN), also referred to as a wireless body area network (WBAN) or a body sensor network (BSN), is a wireless network of computing devices that are associated with a particular human body or a particular person. BAN devices may be embedded inside the body, may be implants, may be surface-mounted on the body in a fixed position (i.e., wearable technology), or may be accompanied devices that humans can carry in different positions, in clothes pockets, by hand, or in various bags (e.g., something akin to a mobile phone or other personal communication device). While there is a trend towards the miniaturization of devices, in particular networks consisting of several miniaturized body sensor units (BSUs) together with a single body central unit (BCU), larger-sized smart devices (e.g., tablets and pads) and other accompanied devices can play an important role in terms of acting as a data hub, data gateway, and/or providing a user interface to view and manage BAN applications.

WBAN technology uses wireless personal area network (WPAN) technologies to implement communications on, near, and/or around the human body. The term BAN has come to refer to systems where communication is entirely within, on, and/or in the immediate proximity of a human body. A WBAN system can use WPAN wireless technologies as gateways to reach longer ranges. Through gateway devices, it is possible to connect the wearable devices on the human body to the Internet, so that data from the BAN can be accessed online by any person or device that has a need to review, use, and/or process the BAN data.

DETAILED DESCRIPTION

Figure 1:
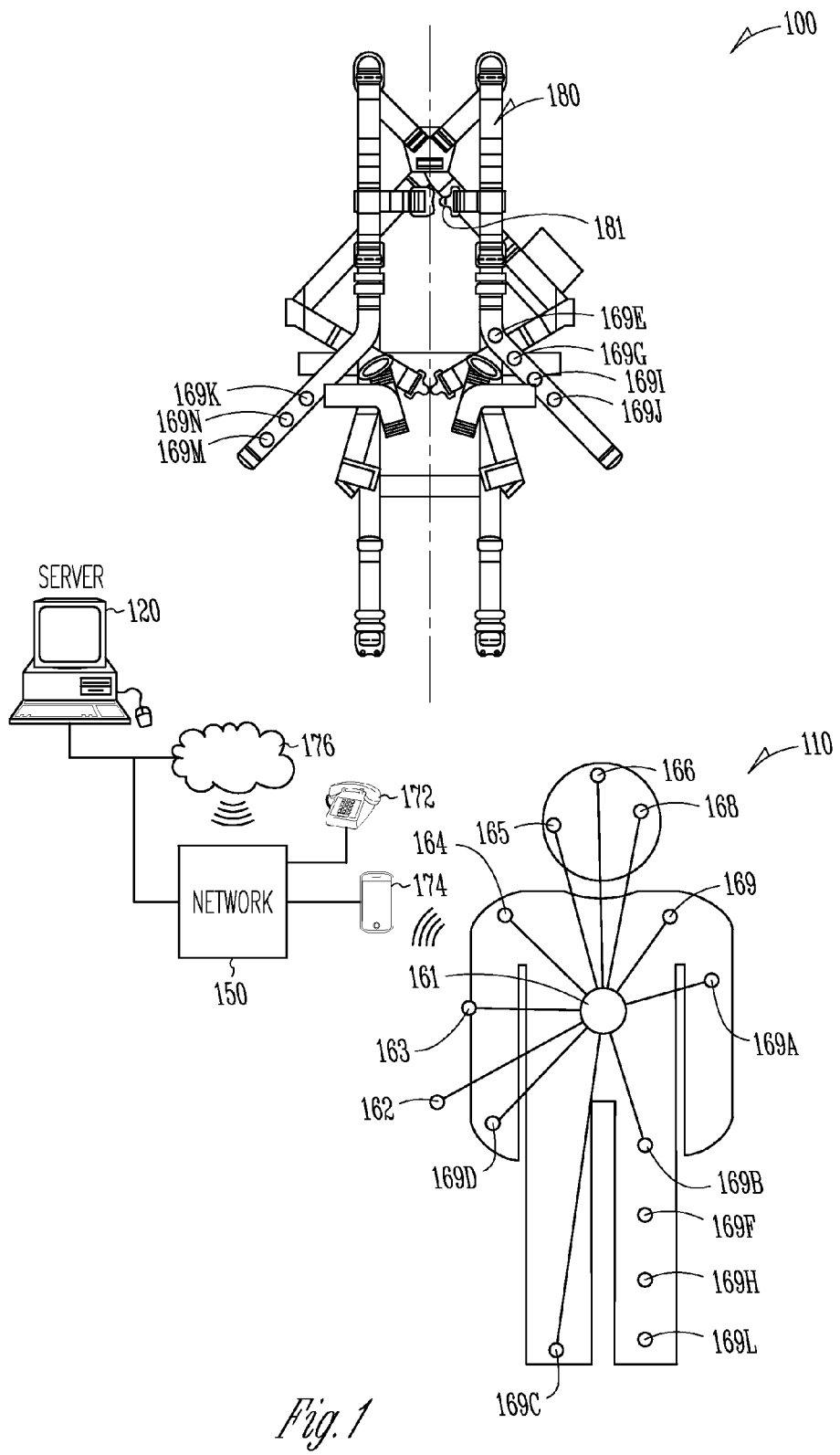
FIG. 1 illustrates a fall protection harness and a body area network.
Figure 2A:
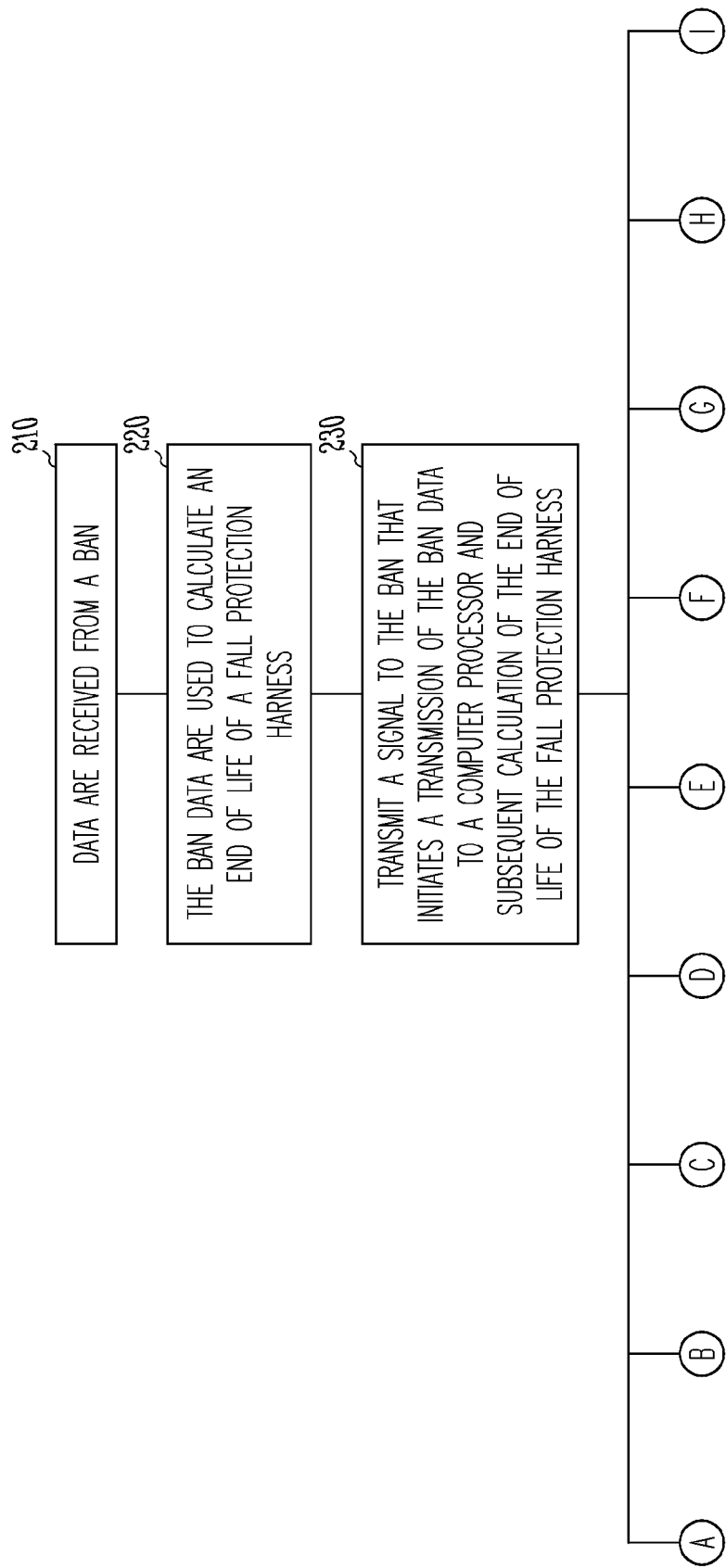
FIGS. 2A-2J are a block diagram illustrating features and operations of a system that monitors a fall protection harness using a body area network.
Figure 2B:
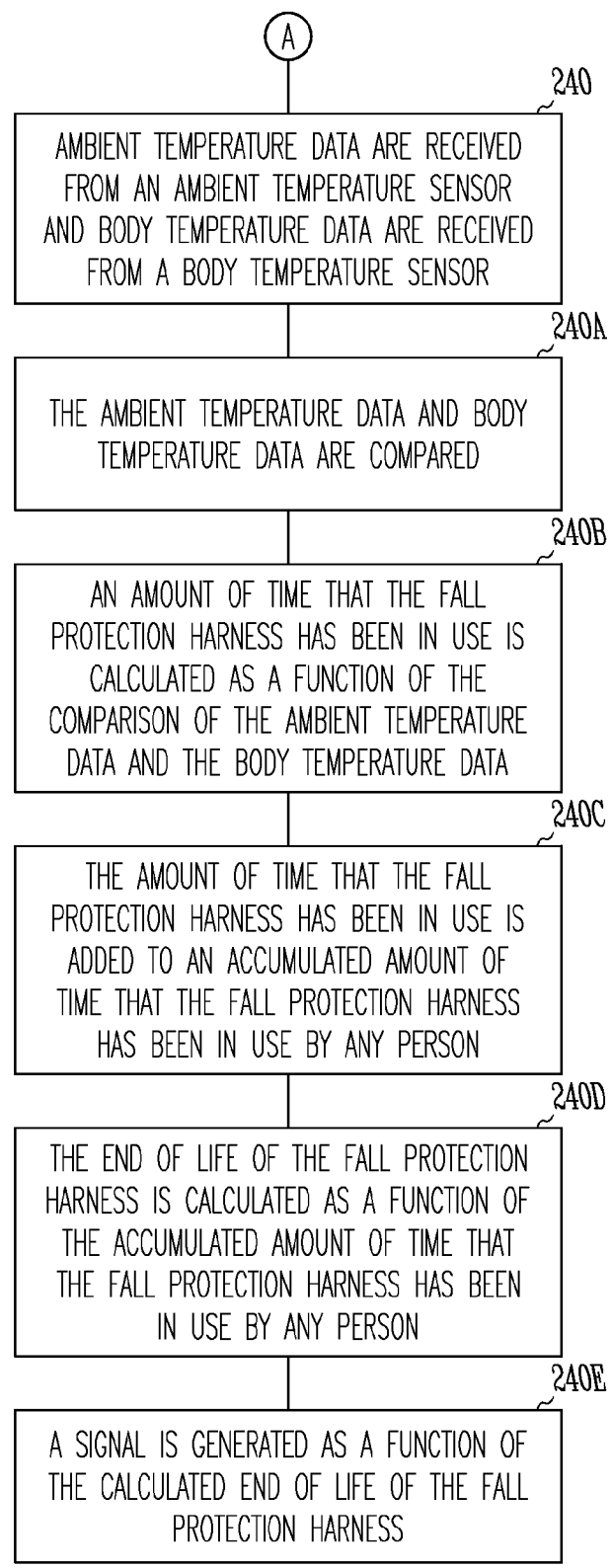
Figure 2C:
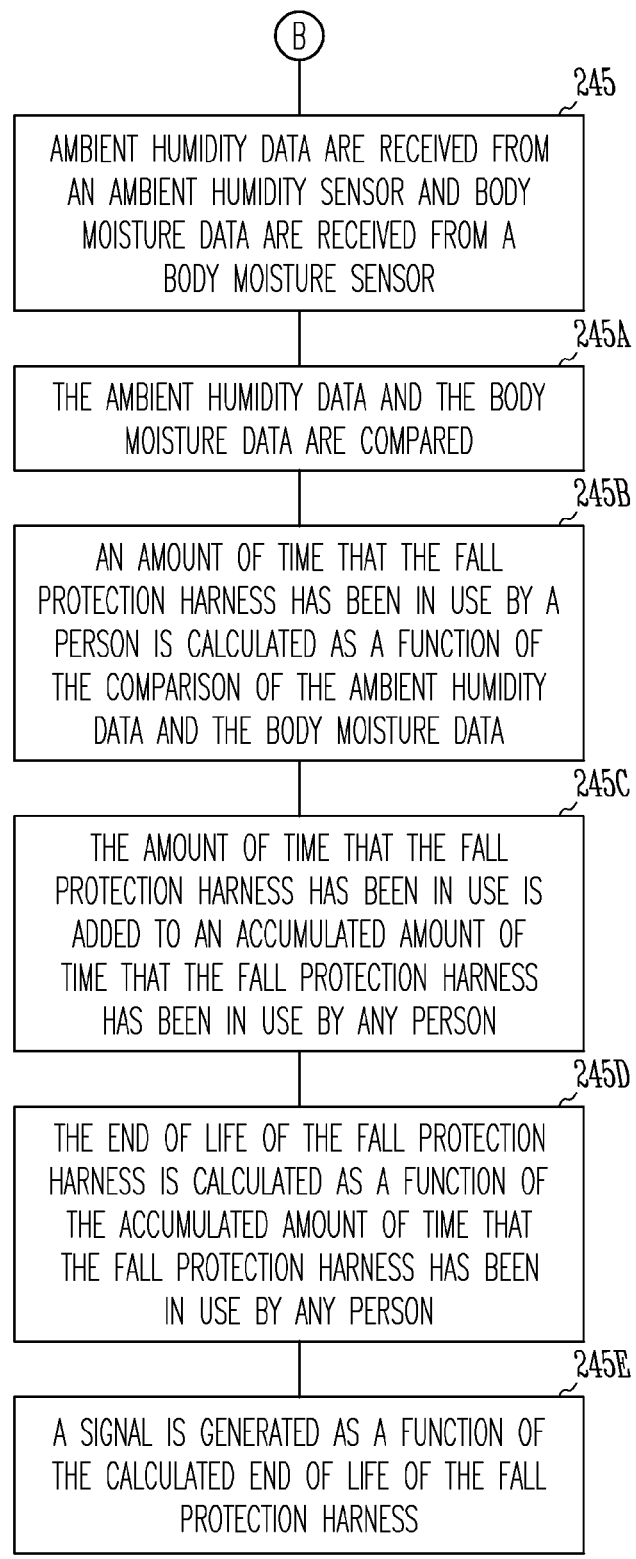
Figure 2D:
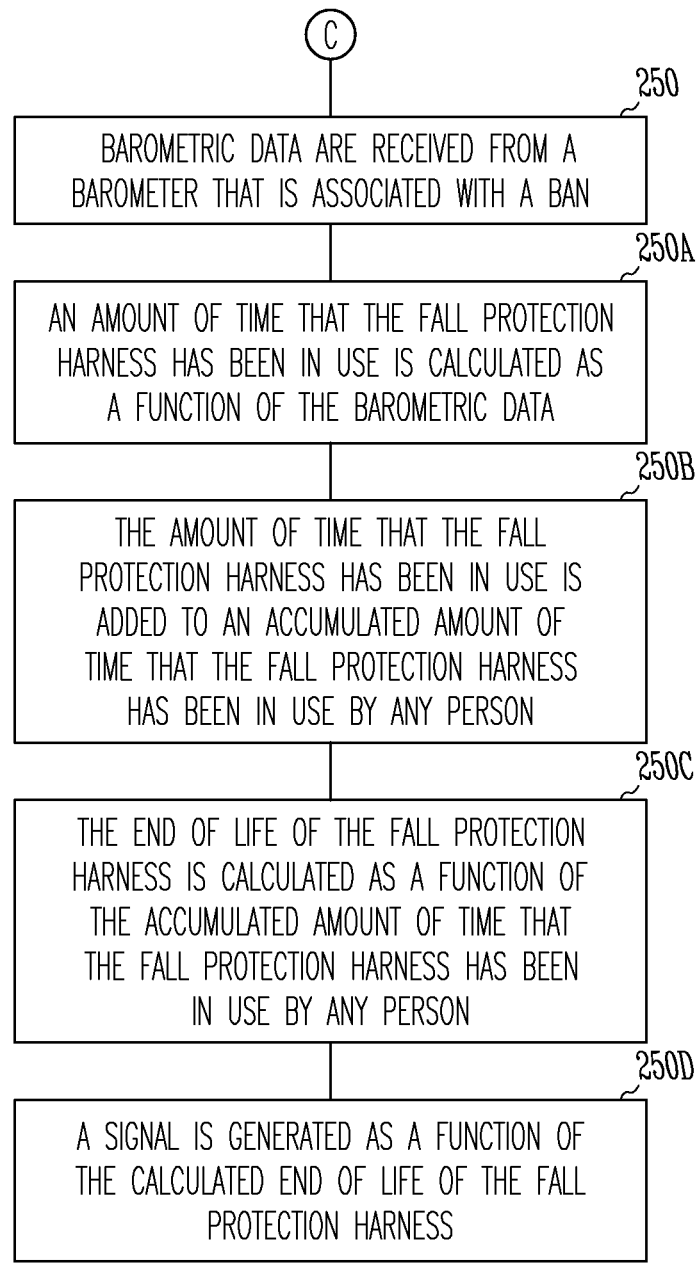
Figure 2E:
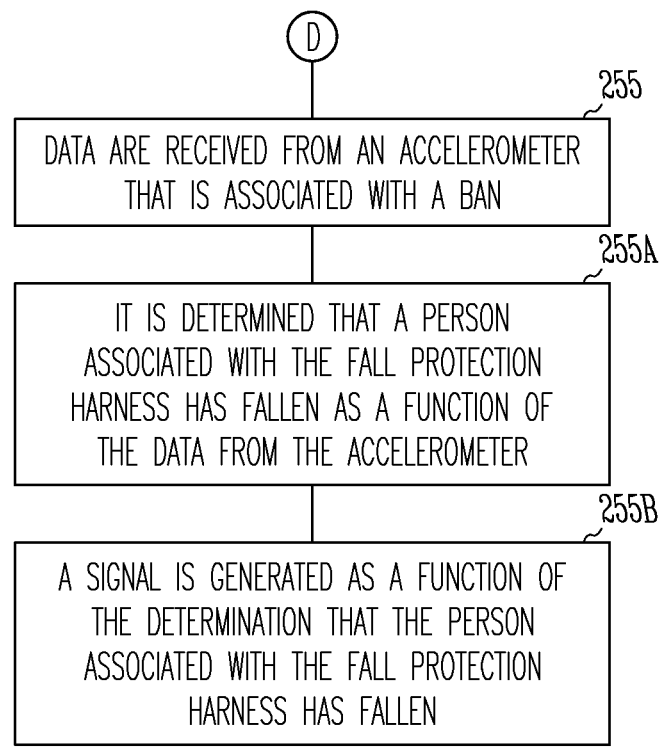
Figure 2F:
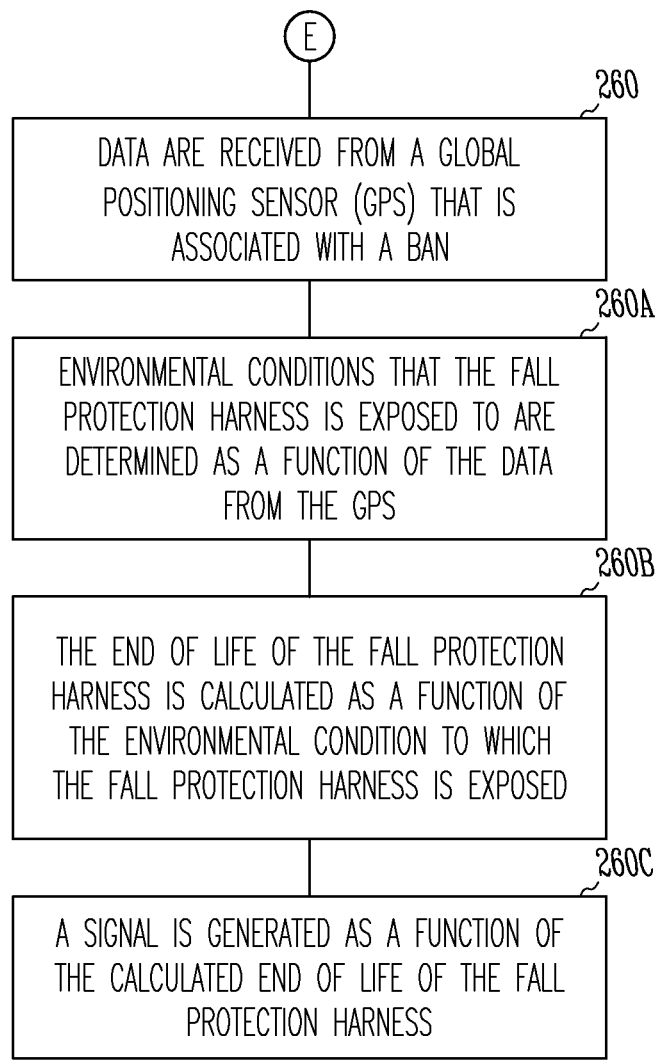
Figure 2G:
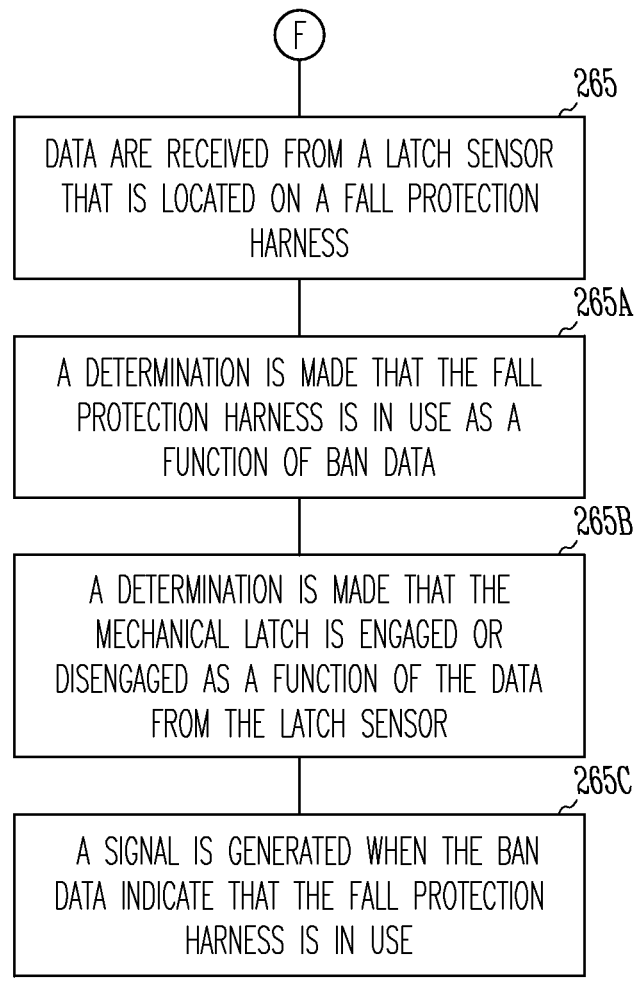
Figure 2H:
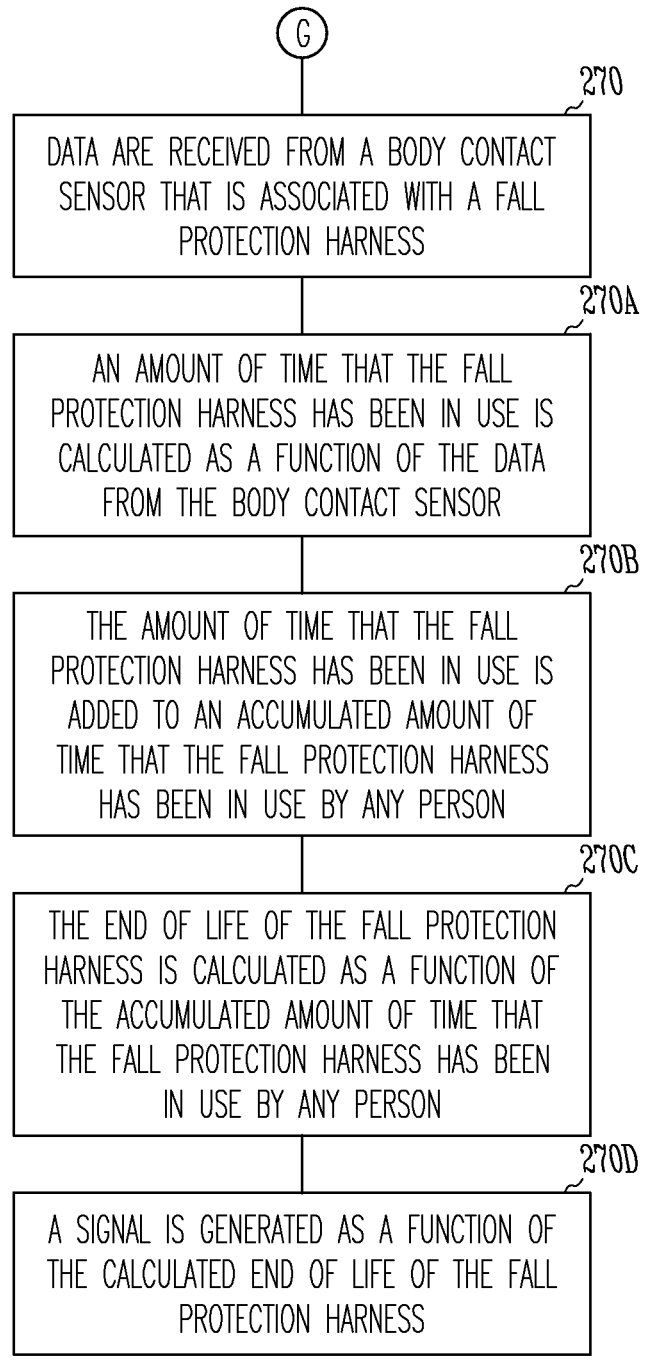
Figure 2I:
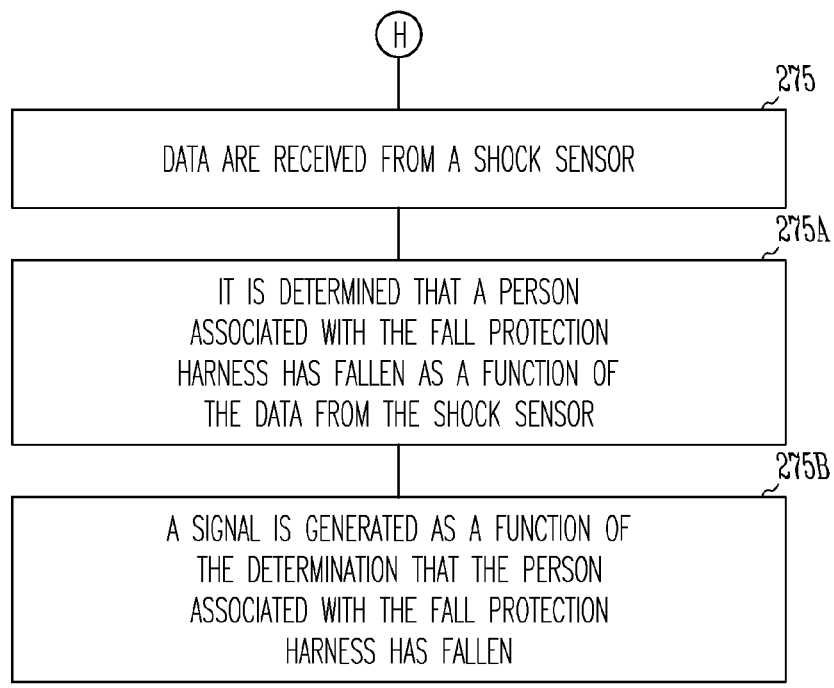
Figure 2J:
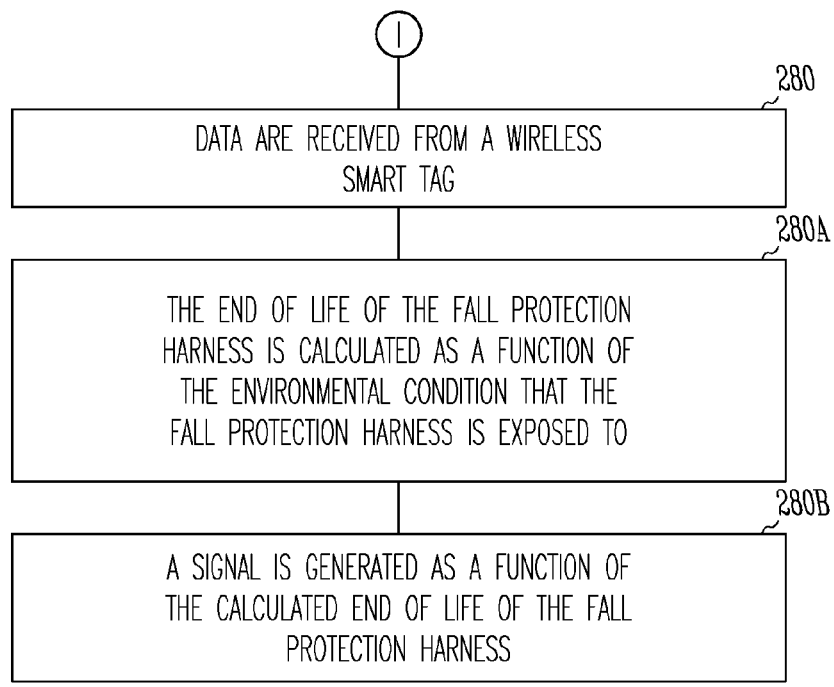

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, electrical, and optical changes may be made without departing from the scope of the present invention. The following description of example embodiments is, therefore, not to be taken in a limited sense, and the scope of the present invention is defined by the appended claims.

The rapid growth in physiological sensors, low-power integrated circuits, and wireless communication has enabled a new generation of wireless sensor networks, now used for purposes such as monitoring traffic, crops, infrastructure, and health. For example, in a typical application, a body area network (BAN) allows inexpensive and continuous health monitoring with real-time updates of medical records through the Internet or other data communications network. A number of intelligent physiological sensors can be embedded in a living body or integrated into a wearable wireless body area network, which can be used for computer-assisted rehabilitation or early detection of medical conditions. Such use of a BAN relies in part on the feasibility of implanting very small biosensors inside a living body that are comfortable and that don't impair normal activities. The implanted sensors in the body collect various physiological changes in order to monitor a being's or patient's health status irrespective of the patient's physical location. The information can be transmitted wirelessly to an external processing unit, which can instantly transmit all information in real time to doctors throughout the world. If an emergency is detected, the physicians can immediately inform the patient through the computer system by sending appropriate messages or alarms. While the level of information provided and energy resources capable of powering the sensors are currently limited because the technology is still in its primitive stage, it is being widely researched and once adopted, is expected to be a breakthrough in healthcare, leading to concepts like telemedicine.

Consequently, initial applications of BANs have been primarily in the healthcare domain, especially for continuous monitoring and logging vital parameters of patients suffering from chronic diseases such as diabetes, asthma, and heart disease. A BAN that is instantiated on a patient can alert medical care professionals, even before the patient experiences a medical condition such as a heart attack, by measuring changes in the patient's vital signs. Similarly, a BAN on a diabetic patient could auto-inject insulin through a pump as soon as the patient's insulin level declines.

A typical BAN or BSN includes vital sign monitoring sensors, a processor, motion detectors (e.g., accelerometers) to help identify the location and position of the monitored individual, and some form of communication to transmit vital sign and motion readings to medical practitioners, care givers, or other person interested in the BAN data. Physiological sensors, such as electrocardiographs (ECG) and saturation of peripheral oxygen ($SpO_2$) sensors, have been developed. Other sensors, such as a blood pressure sensor, an electroencephalograph (EEG) sensor, and a personal digital assistant (PDA) for BSN interface are also potentially applicable.

The present disclosure expands these early, typically health-based uses of a BAN, and in particular, relates to a novel use of a BAN to monitor a fall protection harness and a person who uses the fall protection harness. This use addresses the issue wherein fall protection harnesses and other fall protection equipment are used after their ends of life are reached, thereby addressing safety and liability concerns that are a cause of injury or perhaps casualty to a worker using the fall protection harness. Specifically, a BAN with various types of sensors such as skin moisture, temperature, humidity, accelerometer, barometric pressure, blood pressure, stress, physical shock, mechanical latch, body contact, heart rate sensors is used. The BAN can accumulate hours of usage of a particular fall protection harness, and a network and smart phone or other device can connect the BAN to a smart hub. The smart hub can relay all BAN data to a server via the Internet (e.g., via BLE, 4G, Ethernet, Wi-Fi, etc.). The server with an associate database functions as data storage, a calculator and/or predictor of the end of life of the fall protection harness, a message generator, an alarm generator, an alert annunciator, a rules keeper, etc. An end of life message and/or alert indicator are enabled, registered and distributed to a safety enforcer and worker as fall protection harness life is approached and/or ended.

FIG. 1 is a block diagram of a system 100 that includes a body area network (BAN) 110 and a fall protection harness 180. The system 100 also includes a network 150 that couples the BAN 110 to a server 120. The BAN 110 can be coupled to the network 150 via plain old telephone service (POTS) 172, cellular service 174, and/or a wireless local area network (WLAN) 176.

The BAN 110 includes a processor 161, which can include a transceiver, and one or more sensors. The sensors can include sensors related to DNA/protein analysis 162, blood glucose levels 163, body positioning analysis 164, vision analysis 165 (including pupil and other eye analyses), EEG sensors 166, hearing analysis 168, ECG sensors 169, blood pressure sensors 169A, toxin sensors 169B, implants 169C, a means for fingerprint analysis and identification 169D (e.g., storing fingerprint data in a BAN database and using the fingerprint data from the BAN database to identify the person at an access point), an ambient temperature sensor 169E, a body temperature sensor 169F, an ambient humidity sensor 169G, a body moisture sensor 169H, a barometer 169I, an accelerometer 169J, a global positioning sensor 169K, a body contact sensor 169L, a shock sensor 169M, and a smart tag 169N. As previously noted, these BAN sensors or devices can be embedded inside the body, can be implants, can be surface-mounted on the body in a fixed position (i.e., wearable technology), or may be accompanied devices that humans can carry in different positions, in clothes pockets, by hand, or in various bags (e.g., something akin to a mobile phone or other personal communication device). Similarly, in an embodiment, some of the aforementioned sensors may be attached to the harness 180. For example, the ambient temperature sensor 169E, the ambient humidity sensor 169G, the barometer 169I, the accelerometer 169J, the global positioning sensor 169K, the shock sensor 169M, and the smart tag 169N are attached to the harness 180. The harness further can include a latch sensor 181, which senses when a latch on the harness 180 is engaged and/or disengaged.

FIGS. 2A-2J are a block diagram illustrating operations and features of processes and systems for using a BAN to monitor the status and condition of a fall protection harness and the status and condition of a person using the fall protection harness. FIGS. 2A-2J include a number of process blocks 205-280B. Though arranged substantially serially in the example of FIGS. 2A-2J, other examples may reorder the blocks, omit one or more blocks, and/or execute two or more blocks in parallel using multiple processors or a single processor organized as two or more virtual machines or sub-processors. Moreover, still other examples can implement the blocks as one or more specific interconnected hardware or integrated circuit modules with related control and data signals communicated between and through the modules. Thus, any process flow is applicable to software, firmware, hardware, and hybrid implementations.

At the highest level, at 210, body area network (BAN) data are received from a BAN, and at 220, the BAN data are used to calculate an end of life of a fall protection harness. The reception of the BAN data and the calculation of the end of life of the fall protection harness occurs in a computer processor. In an embodiment, the computer processor is located remotely from the BAN, and as indicated at 230, the computer processor transmits a signal to the BAN, and this signal initiates the transmission of the BAN data to the computer processor, and the subsequent calculation of the end of life of the fall protection harness.

At 240, ambient temperature data are received from an ambient temperature sensor and body temperature data are received from a body temperature sensor. At 240A, the ambient temperature data and body temperature data are compared. At 240B, an amount of time that the fall protection harness has been in use by the person is calculated as a function of the comparison of the ambient temperature data and the body temperature data. If the ambient temperature data and the body temperature data are approximately equal, then this indicates that the fall protection harness is currently being worn by a person (that is, it is in use). The ambient temperature data and the body temperature data will be approximately equal when the fall protection harness is being worn because, for example, when the ambient temperature sensor is attached to the fall protection harness, the body temperature of the person will be sensed by the ambient temperature sensor and cause the ambient temperature sensor to sense a temperature at or around the body temperature. The amount of time that the ambient temperature and body temperature are approximately equal is the amount of time that the fall protection harness has been worn during a particular time period. At 240C, the amount of time that the fall protection harness has been in use by the person is added to an accumulated amount of time that the fall protection harness has been in use by any person. That is, operation 240C accumulates over time the number of hours that the fall protection harness has been in use. At 240D, the end of life of the fall protection harness is calculated as a function of the accumulated amount of time that the fall protection harness has been in use by any person. The end of life calculation can be a simple comparison to an upper limit on the number of hours that a fall protection harness can affectively protect a person from a fall. At 240E, a signal is generated by the computer processor as a function of the calculated end of life of the fall protection harness. Consequently, when a particular fall protection harness exceeds the limit of the number of hours that indicates safe usage, the signal is generated and can be transmitted to an appropriate person or device, thereby alerting the person or device to retire the fall protection harness from use.

At 245, ambient humidity data are received from an ambient humidity sensor and body moisture data are received from a body moisture sensor. At 245A, the ambient humidity data and the body moisture data are compared, and at 245B, an amount of time that the fall protection harness has been in use by a person is calculated as a function of the comparison of the ambient humidity data and the body moisture data. If the ambient humidity data and the body moisture data are approximately equal, then this indicates that the fall protection harness is currently being worn by a person (that is, it is in use). The ambient humidity data and the body moisture data will be approximately equal when the fall protection harness is being worn because, for example, when an ambient humidity sensor is attached to the fall protection harness, the body moisture of the person will be sensed by the ambient humidity sensor, and the ambient humidity data and the body moisture data will tend towards each other. The amount of time that the ambient humidity and body moisture are approximately equal is the amount of time that the fall protection harness has been worn during a particular time period. At 245C, the amount of time that the fall protection harness has been in use by the person is added to an accumulated amount of time that the fall protection harness has been in use by any person. That is, operation 245C accumulates over time the number of hours that the fall protection harness has been in use. At 245D, the end of life of the fall protection harness is calculated as a function of the accumulated amount of time that the fall protection harness has been in use by any person. The end of life calculation can be a simple comparison to an upper limit on the number of hours that a fall protection harness can affectively protect a person. At 245E, a signal is generated as a function of the calculated end of life of the fall protection harness. Consequently, when a particular fall protection harness exceeds the limit of the number of hours that indicates safe usage, the signal is generated and can be transmitted to an appropriate person or device, thereby alerting the person or device that the fall protection harness should be retired from use.

At 250, barometric data are received from a barometer that is associated with a BAN. At 250A, an amount of time that the fall protection harness has been in use by the person is calculated as a function of the barometric data. The basic idea behind this embodiment is that when a person is using a fall protection harness, the worker is at an elevated height compared to a baseline, which can be detected by a slight change in the barometric pressure. For example, when the person with the fall protection harness is moving (climbing stairs, climbing a ladder, going up a lift, etc.), the resultant change in barometric data would indicate that the harness is in use. The amount of time that the barometric pressure is at the level that indicates the elevated level above the baseline is the amount of time that the fall protection harness is in use. In an embodiment, factors that affect the barometric data that are independent of the elevation of the person and the fall protection harness are accounted for. For example, the system can be configured to account for a person, who has the fall protection harness in his possession, driving up a not insubstantial hill to a worksite. To account for such a scenario, GPS data and an accelerometer could be used to identify such situations and then used to filter out data during such times. In another example, barometric change that happens very slowly would most likely be weather-based, and such data would also be filtered out. In yet another embodiment, the barometric data from the BAN is compared with barometric data from a reference, such as a weather station and/or a ground-based barometer. At 250B, the amount of time that the fall protection harness has been in use by the person, as inferred from the barometric data, is added to an accumulated amount of time that the fall protection harness has been in use by any person. That is, operation 250B accumulates over time the number of hours that the fall protection harness has been in use. At 250C, the end of life of the fall protection harness is calculated as a function of the accumulated amount of time that the fall protection harness has been in use by any person. The end of life calculation can be a simple comparison to an upper limit on the number of hours that a fall protection harness can affectively protect a person from a fall. At 250D, a signal is generated as a function of the calculated end of life of the fall protection harness. Consequently, when a particular fall protection harness exceeds the limit of the number of hours that indicates safe usage, the signal is generated and can be transmitted to an appropriate person or device, thereby alerting that the fall protection harness should be retired from use.

At 255, data are received from an accelerometer that is associated with a BAN. At 255A, it is determined that a person associated with the fall protection harness has fallen as a function of the data from the accelerometer. At 255B, a signal is generated as a function of the determination that the person associated with the fall protection harness has fallen. Specifically, if the accelerometer data show a sudden increase in acceleration, shortly followed by a rapid deceleration to zero, then this indicates that the person associated with the fall protection harness may have fallen, and assistance should be dispatched to aid the person.

At 260, data are received from a global positioning sensor (GPS) that is associated with a BAN. At 260A, environmental conditions that the fall protection harness is exposed to are determined as a function of the data from the GPS. For example, if the GPS data indicates that the fall protection harness is used primarily in a hot, dry climate such as in Arizona, the hot dry climate may accelerate the deterioration of the fall protection harness, and such accelerated deterioration should be taken into account in determining the end of life of the fall protection harness. Similarly, the GPS could indicate that the fall protection harness is being used in other harsh conditions such as at a beach site wherein the fall protection harness is exposed to humidity and salt water, or a cliff site where edges of rocks can damage the fall protection harness. At 260B, the end of life of the fall protection harness is calculated as a function of the environmental condition to which the fall protection harness is exposed. The end of life calculation can be a simple comparison to an upper limit on the number of hours that a fall protection harness can affectively protect a person. At 260C, a signal is generated as a function of the calculated end of life of the fall protection harness. Consequently, when a particular fall protection harness exceeds the limit of the number of hours that indicates safe usage, the signal is generated and can be transmitted to an appropriate person or device, thereby alerting the person or device that the fall protection harness should be retired from use.

In an embodiment, a latch sensor is coupled to a mechanical latch of the fall protection harness. The latch sensor determines if the fall protection harness is being used properly. Specifically, at 265, data are received from the latch sensor that is located on the fall protection harness. At 265A, a determination is made that the fall protection harness is in use as a function of the BAN data. For example, as noted above, an ambient temperature sensor and a body temperature sensor can indicate that the fall protection harness is in use. At 265B, a determination is made that the mechanical latch is engaged or disengaged as a function of the data from the latch sensor. At 265C, a signal is generated when the BAN data indicate that the fall protection harness is in use. The signal includes data indicating that the mechanical latch is engaged or disengaged based on the latch sensor data. Consequently, when the BAN data indicate that the fall protection harness is in use, a determination can be made whether the fall protection harness has been properly put into use by examining the latch sensor data. So, if a fall protection harness is in use, but one or more latches are not properly secured, this situation can be brought to the attention a supervisor who can warn the person that his fall protection harness is not properly secured.

At 270, data are received from a body contact sensor that is associated with a fall protection harness. At 270A, an amount of time that the fall protection harness has been in use by one or more persons is calculated as a function of the data from the body contact sensor. For example, the body contact sensor can be placed on the inside of a strap of the fall protection harness so that the body contact sensor will come in contact with a person, and upon putting on the fall protection harness, the body contact sensor will sense this placement. At 270B, the amount of time that the fall protection harness has been in use by the person is added to an accumulated amount of time that the fall protection harness has been in use by any person. Operation 270B accumulates over time the number of hours that the fall protection harness has been in use. At 270C, the end of life of the fall protection harness is calculated as a function of the accumulated amount of time that the fall protection harness has been in use by any person. The end of life calculation can be a simple comparison to an upper limit on the number of hours that a fall protection harness can effectively protect a person. At 270D, a signal is generated as a function of the calculated end of life of the fall protection harness. Consequently, when a particular fall protection harness exceeds the limit of the number of hours that indicates safe usage, the signal is generated and can be transmitted to an appropriate person or device thereby alerting that the fall protection harness should be retired from use.

In an embodiment, the BAN can include a shock sensor. At 275, data are received from the shock sensor. At 275A, it is determined that a person associated with the fall protection harness has fallen as a function of the data from the shock sensor, and at 275B, a signal is generated as a function of the determination that the person associated with the fall protection harness has fallen. Assistance can then be dispatched to the person who has fallen.

In another embodiment, the BAN includes a wireless smart tag. At 280, data are received from the wireless smart tag. The data from the wireless smart tag include indoor location information and an indoor environmental condition that the fall protection harness is exposed to as a function of the data from the wireless smart tag. For example, if the fall protection apparatus is used in an industrial environment that is hot and dry, this may have an effect on the duration of the safe, useable life of the fall protection harness. At 280A, the end of life of the fall protection harness is calculated as a function of the environmental condition that the fall protection harness is exposed to, and at 280B, a signal is generated as a function of the calculated end of life of the fall protection harness. Consequently, when a particular fall protection harness exceeds the limit of the number of hours that indicates safe usage, the signal is generated and can be transmitted to an appropriate person or device, thereby alerting the person or device that the fall protection harness should be retired from use.

It should be understood that there exist implementations of other variations and modifications of the invention and its various aspects, as may be readily apparent, for example, to those of ordinary skill in the art, and that the invention is not limited by specific embodiments described herein. Features and embodiments described above may be combined with each other in different combinations. It is therefore contemplated to cover any and all modifications, variations, combinations or equivalents that fall within the scope of the present invention.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. A system comprising:
   a computer processor operable to:
   receive body area network (BAN) data;
   calculate an end of life of a fall protection harness as a function of the BAN data;
   transmit a signal to a BAN associated with a person;
   receive from the BAN the BAN data; and
   calculate the end of life of the fall protection harness as a function of the BAN data;
   wherein the BAN comprises an accelerometer; and
   wherein the computer processor is operable to:
   receive data from the accelerometer;
   determine that a person associated with the fall protection harness has fallen as a function of the data from the accelerometer; and
   generate a signal as a function of the determination that the person associated with the fall protection harness has fallen.

2. The system of claim 1, wherein the BAN comprises an ambient temperature sensor and a body temperature sensor; and
   wherein the computer processor is operable to:
   receive ambient temperature data from the ambient temperature sensor;
   receive body temperature data from the body temperature sensor;
   compare the ambient temperature data and body temperature data;
   calculate an amount of time that the fall protection harness has been in use by the person as a function of the comparison of the ambient temperature data and the body temperature data;
   add the amount of time that the fall protection harness has been in use by the person to an accumulated amount of time that the fall protection harness has been in use by any person;
   calculate the end of life of the fall protection harness as a function of the accumulated amount of time that the fall protection harness has been in use by any person; and
   generate a signal as a function of the calculated end of life of the fall protection harness.

3. The system of claim 1, wherein the BAN comprises an ambient humidity sensor and a body moisture sensor; and
   wherein the computer processor is operable to:
   receive ambient humidity data from the ambient humidity sensor;
   receive body moisture data from the body moisture sensor;
   compare the ambient humidity data and the body moisture data;
   calculate an amount of time that the fall protection harness has been in use by the person as a function of the comparison of the ambient humidity data and the body moisture data;
   add the amount of time that the fall protection harness has been in use by the person to an accumulated amount of time that the fall protection harness has been in use by any person;
   calculate the end of life of the fall protection harness as a function of the accumulated amount of time that the fall protection harness has been in use by any person; and
   generate a signal as a function of the calculated end of life of the fall protection harness.

4. The system of claim 1, wherein the BAN comprises a barometer; and
wherein the computer processor is operable to:
receive barometric data from the barometer;
calculate an amount of time that the fall protection harness has been in use by the person as a function of the barometric data;
add the amount of time that the fall protection harness has been in use by the person to an accumulated amount of time that the fall protection harness has been in use by any person;
calculate the end of life of the fall protection harness as a function of the accumulated amount of time that the fall protection harness has been in use by any person; and
generate a signal as a function of the calculated end of life of the fall protection harness.

5. The system of claim 1, wherein the BAN comprises a global positioning sensor (GPS); and
wherein the computer processor is operable to:
receive data from the GPS;
determine an environmental condition that the fall protection harness is exposed to as a function of the data from the GPS;
calculate the end of life of the fall protection harness as a function of the environmental condition that the fall protection harness is exposed to; and
generate a signal as a function of the calculated end of life of the fall protection harness.

6. The system of claim 1, comprising a latch sensor coupled to a mechanical latch of the fall protection harness;
wherein the computer processor is operable to:
receive data from the latch sensor;
determine that the fall protection harness is in use as a function of the BAN data;
determine that the mechanical latch is engaged or disengaged as a function of the data from the latch sensor; and
generate a signal when the BAN data indicates that the fall protection harness is in use, the signal indicating that the mechanical latch is engaged or disengaged based on the data from the latch sensor.

7. The system of claim 1, wherein the BAN comprises a body contact sensor; and
wherein the computer processor is operable to:
receive data from the body contact sensor;
calculate an amount of time that the fall protection harness has been in use by the person as a function of the data from the body contact sensor;
add the amount of time that the fall protection harness has been in use by the person to an accumulated amount of time that the fall protection harness has been in use by any person;
calculate the end of life of the fall protection harness as a function of the accumulated amount of time that the fall protection harness has been in use by any person; and
generate a signal as a function of the calculated end of life of the fall protection harness.

8. The system of claim 1, wherein the BAN comprises a shock sensor; and
wherein the computer processor is operable to:
receive data from the shock sensor;
determine that a person associated with the fall protection harness has fallen as a function of the data from the shock sensor; and
generate a signal as a function of the determination that the person associated with the fall protection harness has fallen.

9. The system of claim 1, wherein the BAN comprises a wireless smart tag; and
wherein the computer processor is operable to:
receive data from the wireless smart tag, the data from the wireless smart tag comprising indoor location information and an indoor environmental condition to which the fall protection harness is exposed;
calculate the end of life of the fall protection harness as a function of the environmental condition to which the fall protection harness is exposed; and
generate a signal as a function of the calculated end of life of the fall protection harness.

10. The system of claim 1, wherein the computer processor comprises a server computer processor.

11. The system of claim 1, wherein the BAN comprises a transceiver and one or more sensors.

12. The system of claim 11, wherein the transceiver couples the BAN to the computer processor.

13. The system of claim 1, wherein the BAN data comprise biometric data, and the biometric data are used to calculate the end of life of the fall protection harness.

14. The system of claim 1, wherein the computer processor is positioned on a person and the computer processor is operable to aggregate the BAN data and transmit the BAN data to a server.

15. A system comprising:
a computer processor operable to:
receive body area network (BAN) data;
calculate an end of life of a fall protection harness as a function of the BAN data;
transmit a signal to a BAN associated with a person;
receive from the BAN the BAN data; and
calculate the end of life of the fall protection harness as a function of the BAN data;
wherein the BAN comprises a shock sensor; and
wherein the computer processor is operable to:
receive data from the shock sensor;
determine that a person associated with the fall protection harness has fallen as a function of the data from the shock sensor; and
generate a signal as a function of the determination that the person associated with the fall protection harness has fallen.

* * * * *